(12) United States Patent
Ouchi

(10) Patent No.: US 6,443,943 B1
(45) Date of Patent: Sep. 3, 2002

(54) HANDLING SECTION FOR ENDOSCOPIC TREATMENT TOOL

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/427,591

(22) Filed: Oct. 27, 1999

(30) Foreign Application Priority Data

Oct. 29, 1998 (DE) .......................................... 10-308145

(51) Int. Cl.⁷ ............................................... A61B 17/00
(52) U.S. Cl. ......................................................... 606/1
(58) Field of Search ........................... 606/1, 205, 167, 606/207; 600/106

(56) References Cited

U.S. PATENT DOCUMENTS 3,903,892 A * 9/1975 Komiya .......................... 606/1
6,113,586 A * 9/2000 Ouchi ............................ 606/1
6,123,678 A * 9/2000 Palmer et al. ............... 600/567
6,162,209 A * 12/2000 Gobron et al. ................. 606/1
6,210,398 B1 * 4/2001 Ouchi ............................ 606/1

FOREIGN PATENT DOCUMENTS

JP          2782529          5/1998

* cited by examiner

*Primary Examiner*—John P. Leubecke
(74) *Attorney, Agent, or Firm*—Greenblum & Bernstein, P.L.C.

(57) ABSTRACT

A handling section for an endoscopic treatment tool that permits the manipulation stroke of a manipulating wire to be set or changed to an optimal condition in an easy way. Tubular stopper (8) for restricting the range over which manipulating members (13, 15) are moved in a direction in which manipulating wire members (3, 3a) are pushed into flexible sheath (1) is formed of a nonmetallic material that can be cut with a cutter and loosely fitted over manipulating wire members 3 and 3a as it is detachably mounted to the basal end portion of flexible sheath (1).

7 Claims, 4 Drawing Sheets

HANDLING SECTION FOR ENDOSCOPIC TREATMENT TOOL

BACKGROUND OF THE INVENTION

The present invention relates to a handling section for an endoscopic treatment tool that is used as it is passed through the treatment tool insertion channel of an endoscope.

Endoscopic treatment tools generally have a handling section, a flexible sheath the basal end of which is coupled to the handling section, and a manipulating wire which passes through the flexible sheath to be movable back and forth relative to the flexible sheath.

The basal end of the manipulating wire is coupled to a manipulating member movably provided in the handling section so that the manipulating wire can be moved back and forth through the manipulating member.

If the manipulating wire of the endoscopic treatment tool is pushed into the flexible sheath in a more-than-necessary amount, it buckles to break. A stopper is therefore necessary that restricts the range over which the manipulating wire is pushed into the flexible sheath.

A conventional way to meet this need is shown in FIG. 6; a step 93 is defined within a basal end socket 95 of a flexible sheath 94 to serve as a stopper which is brought into contact with the distal end of a drive rod 92 securely coupled to the distal end of a manipulating wire 91.

A problem with this design is that if the length of the flexible sheath 94 is increased to about 2 m as in the treatment tool used with a colonoscope, the difference between the lengths of the flexible sheath 94 and the manipulating wire 91 is so great as to cause variations in the manipulation stroke S.

If the manipulation stroke S is unduly short, the manipulating wire 91 does not work properly; if the stroke is excessively long, the manipulating wire 91 buckles to break. The same phenomenon occurs if the manipulating wire 91 extends as the result of repeated use of the treatment tool.

Handling sections for endoscopic treatment tools are also characterized in that even ones of an identical type are commonly used with many and various types of treatment tools and that the manipulation stroke S has to be set in accordance with the specific models of such treatment tools. To meet this requirement in the conventional handling section for endoscopic treatment tools that is described above, the position in which the drive rod 92 is secured to the manipulating wire 91 has to be changed but this involves a very complicated operation.

SUMMARY OF THE INVENTION

An object, therefore, of the present invention is to provide a handling section for an endoscopic treatment tool that permits the manipulation stroke of a manipulating wire to be set or changed to an optimal condition in an easy way.

This object can be attained by providing a tubular stopper for restricting the range over which a manipulating member is moved to push a manipulating wire member into a flexible sheath. The tubular stopper is detachably fitted to the basal end portion of the flexible sheath such that the tubular stopper is loosely fitted over the manipulating wire member. If necessary, the stopper is removed, has its length changed and is replaced, whereupon the manipulation stroke of the manipulating wire member can be easily set or changed to an optimal condition.

In a preferable embodiment, a handling section for an endoscopic treatment tool includes:

a main body to which a basal end of a flexible sheath is detachably coupled;

a manipulating member to which a basal end of a manipulating wire member is detachably coupled, the manipulating member being movably arranged on the main body to axially move the manipulating wire member relative to the flexible sheath; and a tubular stopper detachably coupled to the basal end of the flexible sheath and fitted over the manipulating wire member, the tubular stopper restricting a range over which the manipulating member is moved in a direction in which the manipulating wire member is pushed into said flexible sheath.

The tubular stopper is preferably formed of a nonmetallic material that can be cut with a cutter, such as a flexible tube.

The present disclosure relates to the subject matter contained in Japanese patent application No. Hei. 10-308145 (filed on Oct. 29, 1998), which is expressly incorporated herein by reference in its entirety.

DESCRIPTION OF THE PREFERRED EMBODIMENT

An embodiment of the invention is hereunder described with reference to accompanying drawings.

Figure 2:
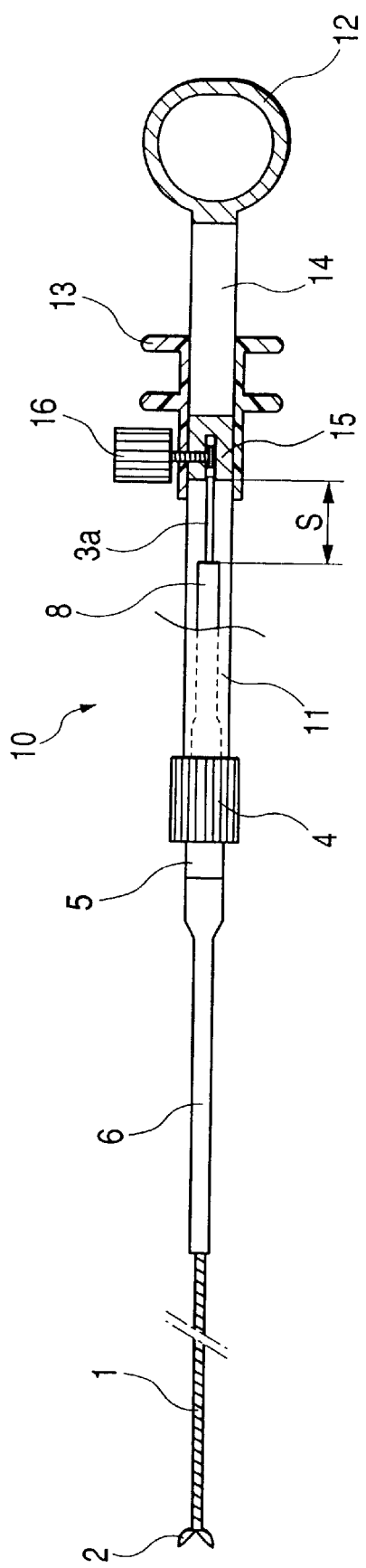
FIG. 2 shows the general layout of an endoscopic treatment tool according to the embodiment of the invention.

FIG. 2 shows biopsy forceps which is used as an endoscopic treatment tool. It has a flexible sheath 1 that is formed of a closely wound coil pipe and is to be slipped into or out of the treatment insertion channel of an endoscope.

A handling section 10 is detachably coupled to the basal end of the flexible sheath 1. A manipulating wire (not shown in FIG. 2) is passed through the flexible sheath 1 so that it is capable of moving back and forth along the longitudinal axis. By manipulating the handling section 10 such that the manipulating wire is moved back and forth, a forceps cup 2 (distal treatment member) that is provided at the distal end of the flexible sheath 1 can be opened or closed remotely.

Shown by 4 is a coupling fixed tube with which a basal socket 5 provided at the basal end of the flexible sheath 1 is detachably retained to the handling section 10, and 6 is an anti-bend tube that ensures that the basal end portion of the flexible sheath 1 does not collapse due to sharp bends.

The main body 11 of the handling section 10 is shaped like a rod and it has a grip ring 12 at the end closer to the operator (surgeon) to receive the operator's thumb. The main body 11 also has a grip spool 13 that receives the forefinger and the middle finger of the operator and which is slidable along the main body 11.

A slit 14 is formed in the main body 11 to extend along the longitudinal axis, and a wire coupling seat 15 is provided within the slit 14 and fixed to the grip spool 13 to be slidably moved along the longitudinal axis together with the grip spool 13.

Shown by 3a is a drive rod that is securely coupled to the basal end of the manipulating wire passed through the flexible sheath 1. The drive rod 3a in combination with the manipulating wire corresponds to the "manipulating wire member" as used in the invention. The grip spool 13 in combination with the wire coupling seat 15 corresponds to the "manipulating member" as used in the invention.

The basal end portion of the drive rod 3a is fixed to the wire coupling seat 15 by means of a manual lock screw 16. Note that the manual lock screw 16 also serves as a terminal to which a high-frequency power supply cord is connectable so that the handling section 10 is also usable with treatment tools that operate on high-frequency current.

Shown by 8 is a tubular stopper that is mounted to the basal socket 5 of the flexible sheath 1. The front end face of the wire coupling seat 15 moves until it contacts the stopper tube 8, thereby restricting the stroke S of the grip spool 13, or the range over which it can be moved to push the drive rod 3a into the basal socket 5 (i.e., in the direction in which the manipulating wire is pushed into the flexible sheath 1).

Figure 1:
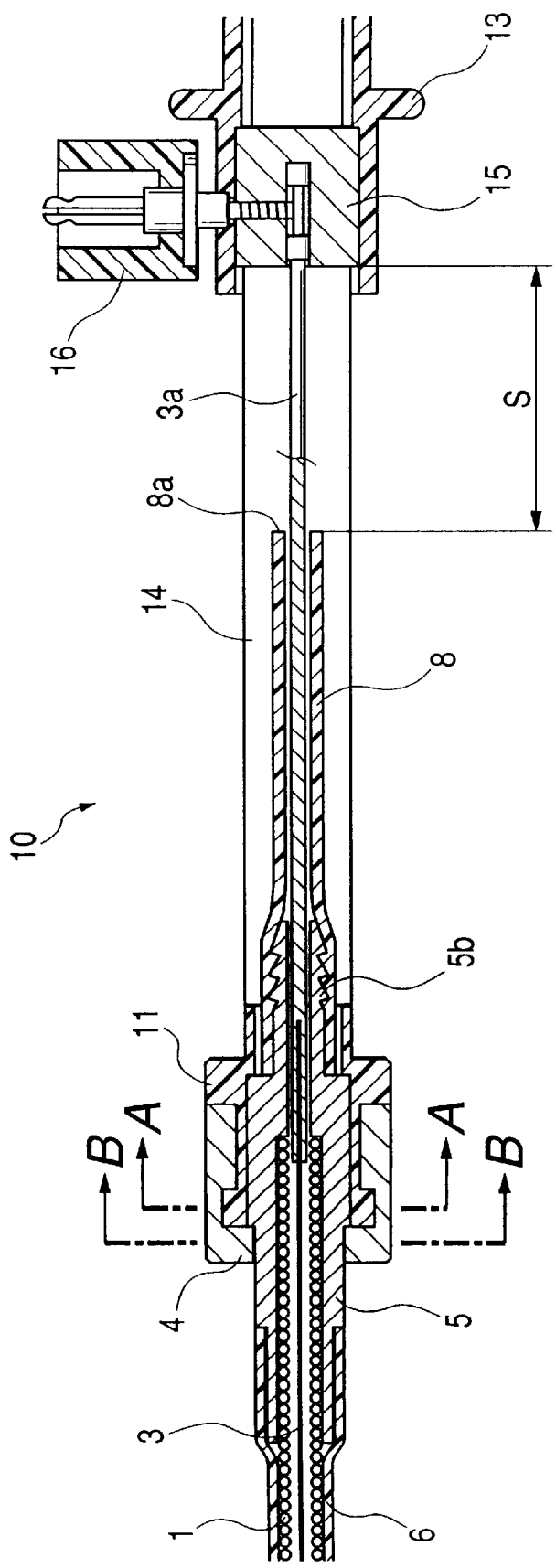
FIG. 1 is a longitudinal section showing enlarged the coupling between a flexible sheath and a handling section for an endoscopic treatment tool according to an embodiment of the invention.

FIG. 1 shows enlarged the coupling between the flexible sheath 1 and the handling section 10, together with the manipulating wire 3 coupled to the drive rod 3a. The coupling fixed tube 4 is mounted to the distal end of the main body 11 of the handling section 10 in such a way that it is not movable along the longitudinal axis but turnable through a certain angle, say, 45 degrees about the longitudinal axis.

Figure 3:
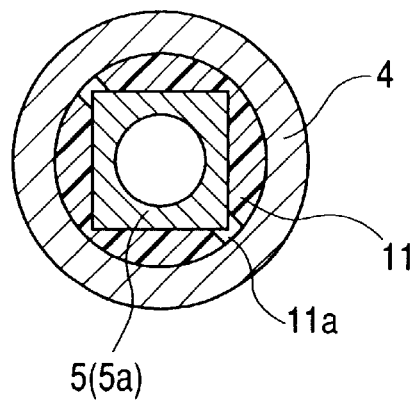
FIG. 3 is section A—A of FIG. 1 according to the embodiment of the invention.

FIG. 3 is section A—A of FIG. 1. As shown, slits 11a are formed in the distal end portion of the main body 11 such that they are parallel to the longitudinal axis and spaced apart typically by an angle of 90 degrees. In the absence of the basal socket 5, the coupling fixed tube 4 can be mounted to the main body 11 by deforming the distal end portion of the main body 11 elastically inward.

Figure 4:
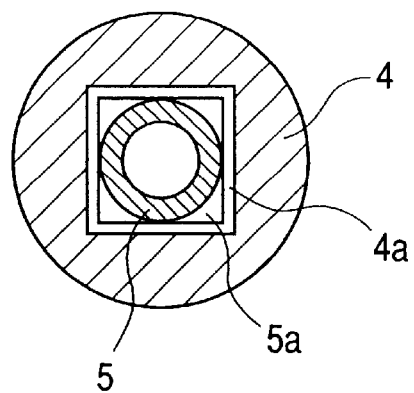
FIG. 4 is section B—B of FIG. 1 according to the embodiment of the invention, with the coupling fixed tube being in a non-fixed state.

FIG. 4 is section B—B of FIG. 1. As shown, the coupling fixed tube 4 has a square hole 4a formed in its front end wall, through which the square shaft portion 5a of the basal socket 5 of the flexible sheath 1 is to be passed. From the front end of the coupling fixed tube 4, the square shaft portion 5a of the basal socket 5 can be fitted into the square hole 4a formed inside of the main body 11.

Figure 5:
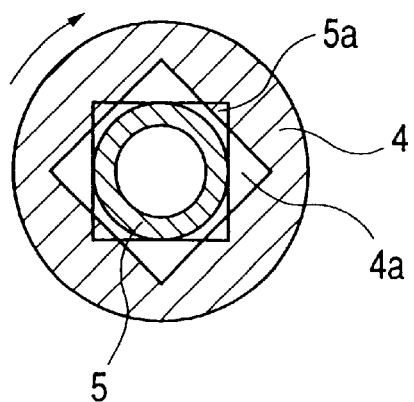
FIG. 5 is section B—B of FIG. 1 according to the embodiment of the invention, with the coupling fixed tube being in a fixed state.
Figure 6:
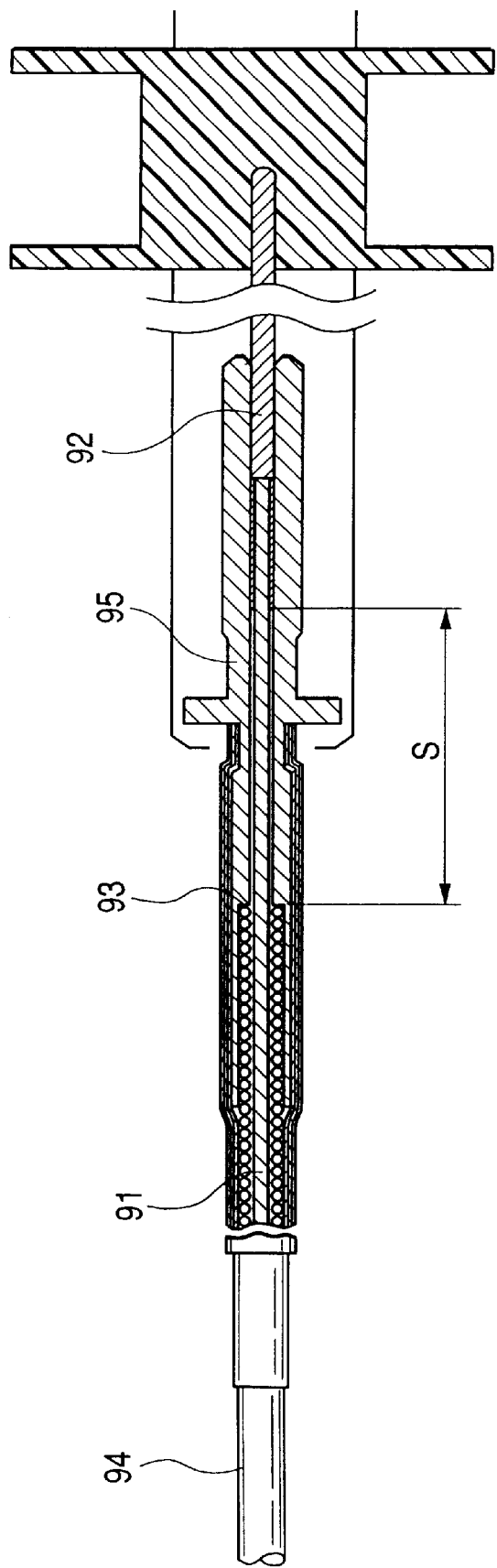
FIG. 6 is a longitudinal section showing the coupling between a flexible sheath and a handling section for a prior art endoscopic treatment tool.

Thus, the basal socket 5 is in detachable engagement with the main body 11 and, as shown in FIG. 5 which is the same section B—B of another state, if the coupling fixed tube 4 is turned through 45 degrees, the square hole 4a in it becomes so oriented that it does not permit the passage of the square shaft portion 5a of the basal socket 5, whereupon the latter is brought into engagement with the main body 11.

The stopper tube 8 is typically formed of a flexible tube such as a polytetrafluoroethylene tube. The stopper tube 8 is securely connected to the tube connecting portion 5b of the basal socket 5 that projects axially backward in a tubular form and the outer surface of which has a saw-toothed cross section. The stopper tube 8 thus connected to the tube connecting portion 5b projects into the slit 14.

In its connection to the stopper tube 8, the tube connecting portion 5b is tightly inserted into the distal end of the stopper tube 8 as the stopper tube 8 is loosely fitted over the drive rod 3a to extend into the slit 14, with the projecting end face 8a forming a stopper face that contacts the wire coupling seat 15.

The handling section for an endoscopic treatment tool according to an embodiment of the invention is constructed in the manner described above. If the coupling fixed tube 4 is turned 45 degrees and the lock screw 16 is loosened by hand, the flexible sheath 1 (and the basal socket 5) together with the manipulating wire 3 (and the drive rod 3a) can be pulled off from the handling section 10 along the longitudinal axis.

The stopper tube 8 can be pulled hard to be disengaged from the tube connecting portion 5b of the basal socket 5. Since the outside diameter of the drive rod 3a is smaller, over the entire length thereof, than the inside diameter of the stopper tube 8, the stopper tube 8 alone (as a single entity) can be easily brought into or out of engagement with the tube connecting portion 5b.

Therefore, if the stopper tube 8 is cut to an optimal length that is appropriate for the treatment tool to be coupled to the handling section 10 and then mounted to the tube connecting portion 5b, the manipulation stroke S of the manipulating wire can be easily set or changed to an optimal condition.

The present invention is by no means limited to the embodiment described above and various modifications may be made, as exemplified by forming the stopper tube 8 as a tubular member that is made of a nonmetallic material that can be cut with a cutter, or mounting the stopper tube 8 to the basal socket 5 by screwing or any other suitable means.

What is claimed is:

1. A handling section connectable to an endoscopic treatment tool having a flexible sheath and a manipulating wire member passed through the flexible sheath axially movably, the handling section comprising:
    a main body to which a basal end of the flexible sheath is detachably coupled;
    a manipulating member to which a basal end of the manipulating wire member is detachably coupled, the manipulating member being movably arranged on the main body to axially move the manipulating wire member relative to the flexible sheath; and
    a tubular stopper detachably coupled to the basal end of the flexible sheath and fitted over the manipulating wire member, the tubular stopper restricting a range over which the manipulating member is moved in a direction in which the manipulating wire member is pushed into said flexible sheath.

2. The handling section according to claim 1, wherein the tubular stopper is formed of a nonmetallic material that can be cut with a cutter.

3. The handling section according to claim 1, wherein said stopper is formed of a flexible tube.

4. The handling section according to claim 1, wherein the main body defines a slit movably receiving the manipulating member therein, and the tubular stopper projects from the basal end of the flexible sheath into the slit.

5. The handling section according to claim 1, wherein an end face of the tubular stopper, which is located opposite from the basal end of the flexible sheath, is contactable with the manipulating member to restrict movement of the manipulating member.

6. The handling section according to claim 5, wherein the end face of the tubular stopper is located within a slit defined by the main body.

7. A handling section connectable to an endoscopic treatment tool having a flexible sheath and a manipulating wire member passed through the flexible sheath axially movably, the handling section comprising:

a main body to which a basal end of the flexible sheath is detachably coupled;

a manipulating member to which a basal end of the manipulating wire member is detachably coupled, the manipulating member being movably arranged on the main body to axially move the manipulating wire member relative to the flexible sheath; and a tubular stopper detachably coupled to the basal end of the flexible sheath and fitted over the manipulating wire member, wherein an end face of the tubular stopper, which is located opposite from the basal end of the flexible sheath, is contactable with the manipulating member to restrict movement of the manipulating member.

* * * * *